(12) United States Patent
Wingen et al.

(10) Patent No.: US 6,515,163 B2
(45) Date of Patent: Feb. 4, 2003

(54) HYDROGENATED PHENANTHRENES AND THEIR USE IN LIQUID-CRYSTAL MIXTURE

(75) Inventors: Rainer Wingen, Hattersheim (DE); Barbara Hornung, Hasselroth (DE); Wolfgang Schmidt, Dreieich (DE)

(73) Assignee: Merck Patent Gesellschaft, Darmstadt (DE)

( * ) Notice: Subject to any disclaimer, the term of this patent is extended or adjusted under 35 U.S.C. 154(b) by 0 days.

(21) Appl. No.: 09/876,222

(22) Filed: Jun. 8, 2001

(65) Prior Publication Data

US 2002/0049348 A1 Apr. 25, 2002

(30) Foreign Application Priority Data

Jun. 8, 2000 (DE) .......................... 100 28 451

(51) Int. Cl.$^7$ .......................... C07C 69/75; C07C 41/00; C09K 19/52; C09K 19/00
(52) U.S. Cl. .......................... 560/8; 560/102; 568/660; 568/661; 570/129; 252/299.01; 252/299.62; 552/544; 428/1.1; 428/1.4
(58) Field of Search ................... 428/1.1, 1.4; 552/544; 252/299.01, 299.62; 570/129; 568/660, 661; 560/8, 102

(56) References Cited

U.S. PATENT DOCUMENTS 5,378,395 A * 1/1995 Weber et al.

* cited by examiner

*Primary Examiner*—Alan Siegel
(74) *Attorney, Agent, or Firm*—Millen, White, Zelano & Branigan, P.C.

(57) ABSTRACT

The invention concerns hydrogenated phenanthrenes of formula I

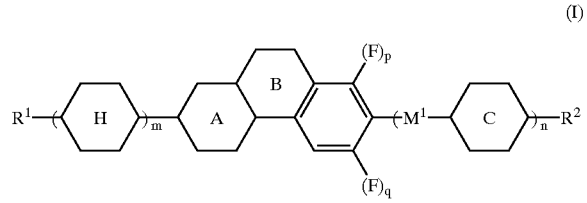

wherein the parameters have the meanings given in the text and their use in liquid crystal compositions.

28 Claims, No Drawings

HYDROGENATED PHENANTHRENES AND THEIR USE IN LIQUID-CRYSTAL MIXTURE

Phenanthrene derivatives for use in liquid-crystalline mixtures have already been disclosed in DE-A 19500768, WO 98/27043, WO 98/27035 or WO 99/24385.

However, since the development of liquid-crystal mixtures can in no way be regarded as complete, display manufacturers are interested in a wide variety of components for mixtures.

In particular, liquid-crystal mixtures are required which have a very broad operating temperature range, but also a very low threshold voltage, for example for use in automobiles, in which a temperature range from −40 to 100° C. can easily occur, but also for portable devices such as mobile telephones and notebook PCs.

There is thus a continuing demand for novel, suitable liquid-crystal mixtures and mixture components.

The present invention thus provides novel components for use in nematic or cholesteric liquid-crystal mixtures which have positive dielectric anisotropy values combined with a favorable viscosity/clearing point ratio. Moreover, the compounds should have a high light and UV stability and thermal stability. They should furthermore be suitable for realizing high voltage holding ratios (VHR). They should also be readily obtainable synthetically and thus potentially inexpensive.

It has now been found that these requirements are satisfied by hydrogenated phenanthrenes of the formula (I)

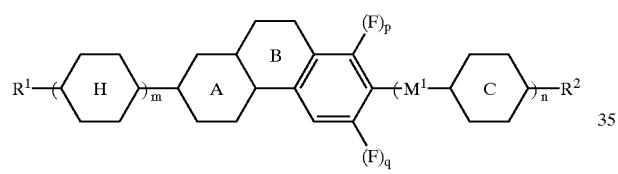

in which:
- $R^1$ is H, an alkyl radical having 1 to 12 carbon atoms or an alkenyl radical having 2 to 8 carbon atoms, where, in each case, one (nonterminal) —CH$_2$— group may be replaced by —O—, —C(=O)O— or —OC(=O) and/or one or more H may be replaced by F,
- $R^2$ is H, F, an alkyl or alkoxy radical having 1 to 12 carbon atoms or an alkenyl or alkenyloxy radical having 2 to 8 carbon atoms, where, in each case, one (nonterminal) —CH$_2$— group may be replaced by —O— or —C(=O)O— and/or one or more H may be replaced by F,
- $M^1$ is —C(=O)O—, —OC(=O)—, —CH$_2$O—, —OCH$_2$—, —C≡C—, —CH$_2$CH$_2$ or a single bond,
- m, n are each, independently of one another, zero or 1; m+n being 0 or 1,
- p, q are each, independently of one another, zero or 1; p+q being 1 or 2,

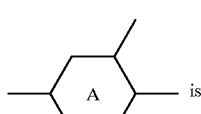

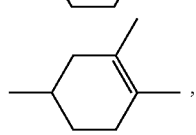

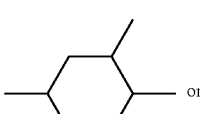

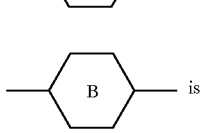

Preference is given to the compounds of the formulae (Ia) to (Im):

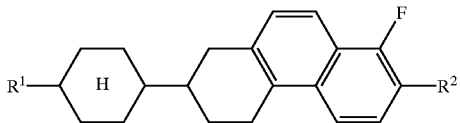
(Ia)

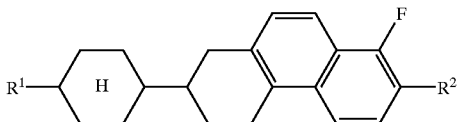
(Ib)

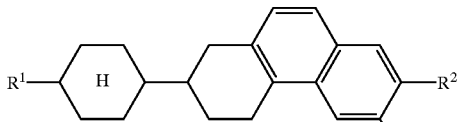
(Ic)

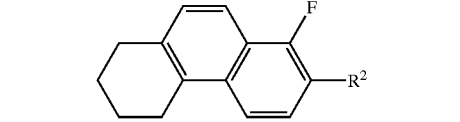
(Id)

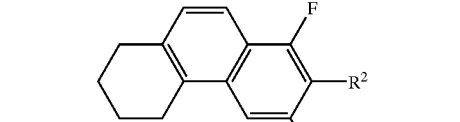
(Ie)

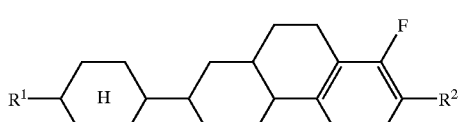
(If)

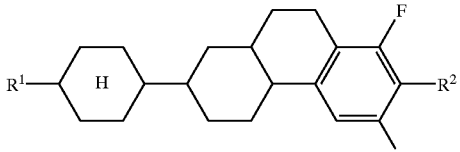
(Ig)

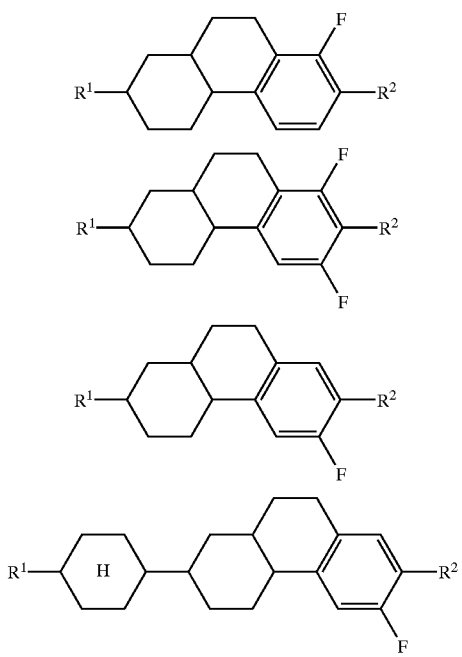

When designating the compounds, the letters j and l were omitted since they might be confused with i and I.

Very particular preference is given to those compounds of the formulae (Ia), (Ib), (Ie), (Ig), (Ih), (Ii) and (Ik) in which $R^2$ is:

a) F, b) an alkyl or alkyloxy radical having 1 to 2 carbon atoms in which one or more H are replaced by F, or c) an alkenyl or alkenyloxy radical having 2 carbon atoms in which one or more H are replaced by F.

Special preference is given to the compounds of the formulae (Ii1), (Ig1), (Ib1) and (Ie1)

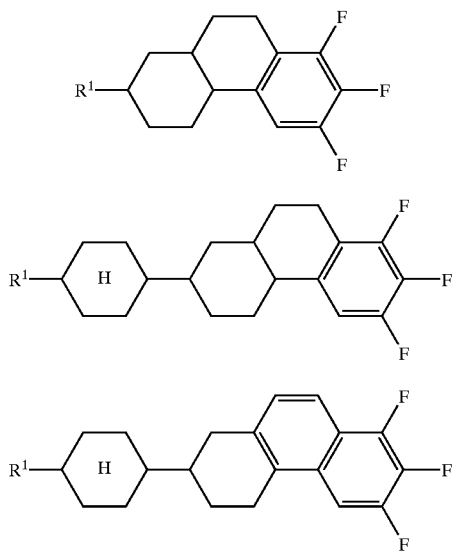

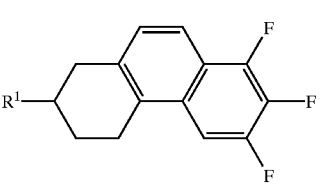

The compounds of the formula (I) are used in liquid-crystal mixtures, preferably in nematic or cholesteric liquid-crystal mixtures. The liquid-crystal mixtures of the invention comprise at least one compound of the formula (I), preferably in an amount of 1 to 40% by weight, based on the liquid-crystal mixture. They preferably comprise at least 3 further components. The invention also provides a liquid-crystal display containing these liquid-crystal mixtures.

Typical liquid crystal mixtures are disclosed in, e.g., U.S. Pat. No. 5,378,395. Typical displays, in which these mixtures are used are AMD displays, e.g., TN-TFT displays, IPS-TFT displays and VAN-TFT displays, among various others.

The compounds of the invention can be prepared as follows:

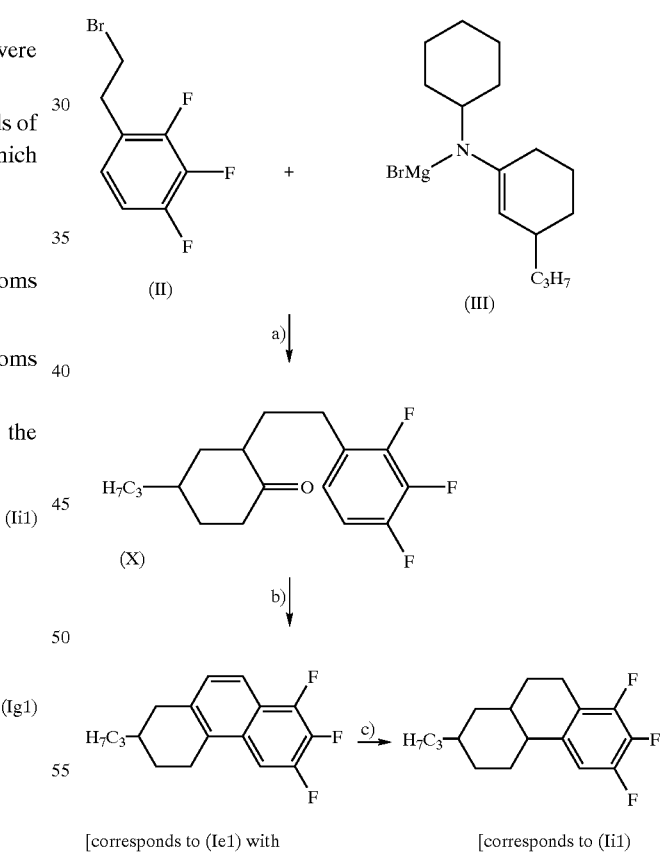

a) [similarly to the method of G. Stork, S. Dowd, J. Am. Chem. Soc. 85, 2178 (1963)]
b) polyphosphoric acid [similarly to the method of R. G. Harvey, M. Halonen, Can. J. Chem. 45, 2630 (1967)]
c) $H_2$/Pd [similarly to the method of P. N. Rylander, Hydrogenation Methods, Academic Press, London, 1985, p. 53]

The synthesis according to Scheme 1 as illustrated for a specific compound can be applied broadly to the synthesis of the compounds according to the invention by varying the fluoro compound (II) or the alkyl chains of the cyclohexy-lamino compounds (III) or by replacing the alkyl substituent in (III) by a 4-alkylcyclohexyl radical.

For example, replacement of 2-(2,3,4-trifluoro-phenyl) ethyl bromide (prepared similarly to the method of R. P. Houghton, M. Voyle, R. Price, J. Chem. Soc. Perkin Trans 1 (1984), 92 5) by 2-(2,3-difluoro-phenyl)ethyl bromide [126163-29-9] may lead to compounds of the formula (Id) or (Ih) in which $R^2$ is F; likewise, compounds of the formula (Id) or (Ih) in which $R^2$ =H can be obtained by using 2-(2-fluoro-phenyl)ethyl bromide [91319-54-9] as (II). The subsequent ortho metalation reactions described below can be applied to the compounds obtained.

Process variations for the synthesis of intermediate (X) are described in T. Cuvigny, H. Normant, Organometallics Chem. Synth., 1 (1971) 237, and T. Takeda, H. Taguchi, T. Fujiwara, Tetrahedron Lett. 41 (2000) 65.

Another possible synthesis route, likewise illustrated for a specific compound, is shown in Scheme 2. However, those skilled in the art will recognize that replacement of the fluorinated tetralone (IV) [1101931-79-8] by 7-fluoro-1-tetralone [2840-44-0] will lead to compounds of the formula (Ik) or (Im), while compounds of the formula (Ih) or (If) can be obtained by using 5-fluoro-1-tetralone [93742-85-9]. It is also known that the substituent $R^1$ of the compounds according to the invention can be varied by varying the alkyl halide in reaction step d).

Starting from (V), those skilled in the art can introduce the substituent $R^2$ in the form of an alkyl group in accordance with standard ortho metalation methods, e.g. using "Schlosser base"; alternatively, the lithium compound which is initially formed can be converted into the corresponding boronic acid by means of boric esters, and this boronic acid can in turn be oxidized to give the corresponding 2-hydroxyphenanthrene derivative. The latter can be transformed by Williamson ether synthesis into compounds of the formula (Ii) [or, similarly, (Ig)] in which $R^2$ is an alkyloxy group; compounds of the formula (I) in which $M^1$ is —OC(=O)— can be obtained by esterification.

Scheme 2

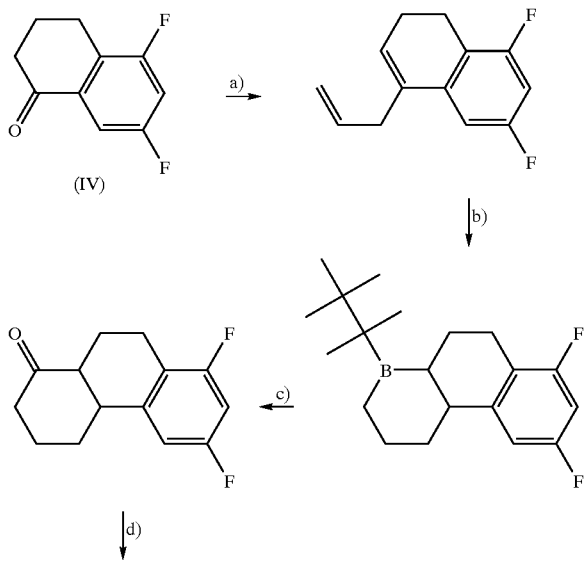

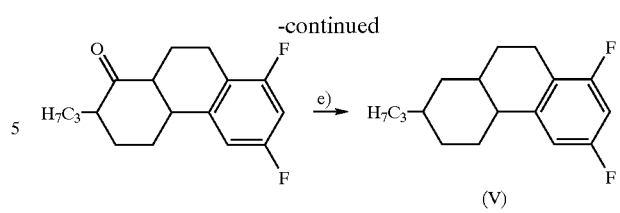

[corresponds to (Ii)
with $R^1$=$C_3H_7$ and $R^2$=H]

a) 1. $H_2C$=$CHCH_2MgBr$
2. $H_2O$ 3. $H_3PO_4$ [similarly to the method of M. Mohammadi, G. W. Kabalka, R. D. Finn, J.Lab. Compds. Radiopharm. XXIV, 317 (1987)]
b) thexylborane [similarly to the method of M. Mohammadi, G. W. Kabalka, R. D. Finn, J. Lab. Compds. Radiopharm. XXIV, 317 (1987)]
c) 1. NaCN 2. TFAA 3. NaOH/$H_2O_2$ [similarly to the method of M. Mohammadi, G. W. Kabalka, R. D. Finn, J. Lab. Compds. Radiopharm. XXI V, 317 (1987)]
d) 1. LDA 2. n-propyl bromide [similarly to the method of M. Mohammadi , G. W. Kabalka, R. D. Finn, J. Lab. Compds. Radiopharm. XXIV, 317 (1987)]
e) e.g. $Et_3SiH$/TFA Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius; and, unless otherwise indicated, all parts and percentages are by weight.

The entire disclosure of all applications, patents and publications, cited above or below, and of corresponding German application No. 100 28 451.5, filed Jun. 8, 2000, is hereby incorporated by reference.

All temperature differences are difference degrees Celsius. All physical properties are given for 20° C., the refractive indices are given for a wavelength of 589 nm, and the dielectric anisotropies are given for a frequency of 1 kHz.

EXAMPLES

Example 1

6,8-Difluoro-7-pentyl-2-propyl-1,2,3,4,4a,9,9a,10-octahydrophenanthrene

A solution of 5, 7-difluoro-1-tetralone [110931-79-8] (prepared in accordance with DE-A 3702039) in tetrahydrofuran is added to an equimolar amount of an allylmagnesium bromide solution in ether at 0° C. The reaction mixture is subjected to conventional aqueous acidic workup (Mohammadi et al., J. Lab. Cpd. Radiopharm. XXIV, 317 (1987)) and distillation. The 5,7-difluoro-1-(1-propen-3-yl)-3,4-dihydronaphthalene obtained is reacted with an equimolar amount of thexyl-borane in terahydrofuran to give B-thexyl6,8-difluoro-2,3,4,4a,9,9a,10-octahydro-1-boraphenanthrene which is reacted with equimolar amounts of sodium cyanide at room temperature without further characterization. After 2 h, an equimolar amount of trifluoroacetic anhydride (TFAA) is added dropwise at −75° C., and the mixture is brought to room temperature with stirring. 3 equivalents of NaOH are added and the mixture is oxidized with 50% $H_2O_2$, finally at 50° C.; extraction and chromatography yield 1-keto6,8-difluoro-1,2,3,4,4a,9,9a,10-octahydrophenanthrene. As described by Mohammadi et al., J. Lab. Cpd. Radiopharm. XXIV, 317 (1987), this product can be converted into 1-keto-6,8-difluoro-2-propyl-1,2,3,4,4a,9,9a,10-octahydrophenanthrene by reacting with lithium diisopropylamide (LDA) followed by addition of n-propyl bromide. This product can be converted into 6,8-difluoro-1,2,3,4,4a,9,9a,10-octahydrophenanthrene by reducing with triethylsilane in trifluoroacetic acid. 6,8-Di-fluoro-7-pentyl-2-propyl-1,2,3,4,4a,9,9a,10-octahydrophenanthrene is obtained by ortho metalation using "Schlosser base" (i.e. butyllithium and potassium tert-butylate; see, for example: F. Mongin, M. Schlosser, Tetrahedron Lett. 1996, 37, 6551-6554) at −75° C., quenching with n-pentyl bromide and conventional workup by hydrolysis, extraction, chromatography (silica gel, dichloromethane) and repeated recrystallization (to increase the proportion of the desired isomer, among other things).

Example 2

A nematic test mixture MLC-9000-100 (from Merck KGaA, Darmstadt, Germany) is admixed with 5% of the compound of Ex. 1; the following improvements are obtained in comparison with the values of the mixture MLC-9000-100 given in parentheses:

clearing point (T(N,I))=92.5° C. (90.5° C.) rotational viscosity ($\gamma_1$)=196 mPas (201 mPas) birefringence ($\Delta n$)=0.1105 (0.1137).

Examples 3 to 28

The following compounds are prepared as depicted in Scheme 1. These compounds have the properties shown in the following table.

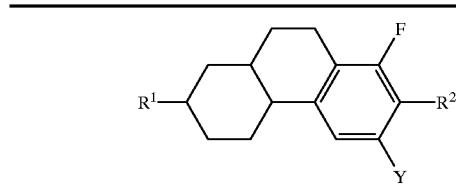

| No. | $R^1$ | Y | $R^2$ | $\Delta n$ | $\Delta \epsilon$ |
|---|---|---|---|---|---|
| 3 | $CH_3$ | H | F | | |
| 4 | $C_2H_5$ | H | F | | |
| 5 | $n$-$C_3H_7$ | H | F | | |
| 6 | $n$-$C_4H_9$ | H | F | | |
| 7 | $n$-$C_5H_{11}$ | H | F | | |
| 8 | $n$-$C_6H_{13}$ | H | F | | |
| 9 | $n$-$C_7H_{15}$ | H | F | | |
| 10 | $CH_3O$ | H | F | | |
| 11 | $C_2H_5O$ | H | F | | |
| 12 | $n$-$C_3H_7O$ | H | F | | |
| 13 | $CH_2$=CH | H | F | | |
| 14 | $CH_3$—CH=CH | H | F | | |
| 15 | $CH_3$ | F | F | | |
| 16 | $C_2H_5$ | F | F | | |
| 17 | $n$-$C_3H_7$ | F | F | 0.081 | 14.6 |
| 18 | $n$-$C_4H_9$ | F | F | | |
| 19 | $n$-$C_5H_{11}$ | F | F | | |
| 20 | $n$-$C_6H_{13}$ | F | F | | |
| 21 | $n$-$C_7H_{15}$ | F | F | | |
| 22 | $CH_3O$ | F | F | | |
| 23 | $C_2H_5O$ | F | F | | |
| 24 | $n$-$C_3H_7O$ | F | F | | |
| 25 | $CH_2$=CH | F | F | | |
| 26 | $CH_3$—CH=CH | F | F | | |
| 27 | $n$-$C_3H_7$ | F | $OCF_3$ | | |
| 28 | $n$-$C_3H_7$ | F | $OCF_3$ | | |

Examples 29 to 54

The following compounds are prepared as depicted in Scheme 1. These compounds have the properties shown in the following table.

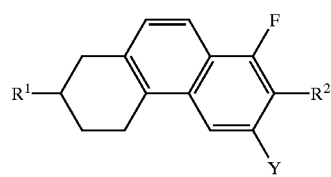

| No. | $R^1$ | Y | $R^2$ | $\Delta n$ | $\Delta \epsilon$ |
|---|---|---|---|---|---|
| 29 | $CH_3$ | H | F | | |
| 30 | $C_2H_5$ | H | F | | |
| 31 | $n$-$C_3H_7$ | H | F | | |
| 32 | $n$-$C_4H_9$ | H | F | | |
| 33 | $n$-$C_5H_{11}$ | H | F | | |
| 34 | $n$-$C_6H_{13}$ | H | F | | |
| 35 | $n$-$C_7H_{15}$ | H | F | | |
| 36 | $CH_3O$ | H | F | | |
| 37 | $C_2H_5O$ | H | F | | |
| 38 | $n$-$C_3H_7O$ | H | F | | |
| 39 | $CH_2$=CH | H | F | | |
| 40 | $CH_3$—CH=CH | H | F | | |
| 41 | $CH_3$ | F | F | | |
| 42 | $C_2H_5$ | F | F | | |
| 43 | $n$-$C_3H_7$ | F | F | | |
| 44 | $n$-$C_4H_9$ | F | F | | |
| 45 | $n$-$C_5H_{11}$ | F | F | 0.139 | 17.3 |
| 46 | $n$-$C_6H_{13}$ | F | F | | |
| 47 | $n$-$C_7H_{15}$ | F | F | | |
| 48 | $CH_3O$ | F | F | | |
| 49 | $C_2H_5O$ | F | F | | |
| 50 | $n$-$C_3H_7O$ | F | F | | |
| 51 | $CH_2$=CH | F | F | | |
| 52 | $CH_3$—CH=CH | F | F | | |
| 53 | $n$-$C_3H_7$ | H | $OCF_3$ | | |
| 54 | $n$-$C_3H_7$ | F | $OCF_3$ | | |

Examples 55 to 83

The following compounds are prepared as described in Example 3. These compounds have the properties shown in the following table.

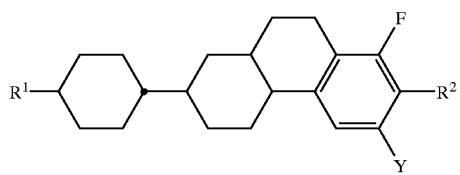

| No. | $R^1$ | Y | $R^2$ | $\Delta n$ | $\Delta \epsilon$ |
|---|---|---|---|---|---|
| 55 | $CH_3$ | H | F | | |
| 56 | $C_2H_5$ | H | F | | |
| 57 | $n$-$C_3H_7$ | H | F | | |
| 58 | $n$-$C_4H_9$ | H | F | | |
| 59 | $n$-$C_5H_{11}$ | H | F | | |
| 60 | $n$-$C_6H_{13}$ | H | F | | |
| 61 | $n$-$C_7H_{15}$ | H | F | | |
| 62 | $CH_3O$ | H | F | | |
| 63 | $C_2H_5O$ | H | F | | |
| 64 | $n$-$C_3H_7O$ | H | F | | |
| 65 | $CH_2$=OH | H | F | | |
| 66 | $CH_3$—CH=CH | H | F | | |
| 67 | $CH_3$ | F | F | | |
| 68 | $C_2H_5$ | F | F | | |
| 69 | $n$-$C_3H_7$ | F | F | | |
| 70 | $n$-$C_4H_9$ | F | F | | |
| 71 | $n$-$C_5H_{11}$ | F | F | 0.081 | 11.0 |

-continued

| No. | R¹ | Y | R² | Δn | Δε |
|---|---|---|---|---|---|
| 72 | n-C₆H₁₃ | F | F | | |
| 73 | n-C₇H₁₅ | F | F | | |
| 74 | CH₃O | F | F | | |
| 78 | C₂H₅O | F | F | | |
| 79 | n-C₃H₇O | F | F | | |
| 80 | CH₂=CH | F | F | | |
| 81 | CH₃—CH=CH | F | F | | |
| 82 | n-C₃H₇ | F | OCF₃ | | |
| 83 | n-C₃H₇ | F | OCF₃ | | |

Examples 84 to 109

The following compounds are prepared as described in Example 29. These compounds have the properties shown in the following table.

| No. | R¹ | Y | R² | Δn | Δε |
|---|---|---|---|---|---|
| 84 | CH₃ | H | F | | |
| 85 | C₂H₅ | H | F | | |
| 86 | n-C₃H₇ | H | F | | |
| 87 | n-C₄H₉ | H | F | | |
| 88 | n-C₅H₁₁ | H | F | | |
| 89 | n-C₆H₁₃ | H | F | | |
| 90 | n-C₇H₁₅ | H | F | | |
| 91 | CH₃O | H | F | | |
| 92 | C₂H₅O | H | F | | |
| 93 | n-C₃H₇O | H | F | | |
| 94 | CH₂=CH | H | F | | |
| 95 | CH₃—CH=CH | H | F | | |
| 96 | CH₃ | F | F | | |
| 97 | C₂H₅ | F | F | | |
| 98 | n-C₃H₇ | F | F | 0.132 | 15.2 |
| 99 | n-C₄H₉ | F | F | | |
| 100 | n-C₅H₁₁ | F | F | | |
| 101 | n-C₆H₁₃ | F | F | | |
| 102 | n-C₇H₁₅ | F | F | | |
| 103 | CH₃O | F | F | | |
| 104 | C₂H₅O | F | F | | |
| 105 | n-C₃H₇O | F | F | | |
| 106 | CH₂=CH | F | F | | |
| 107 | CH₃—CH=CH | F | F | | |
| 108 | n-C₃H₇ | F | OCF₃ | | |
| 109 | n-C₃H₇ | F | OCF₃ | | |

Unless explicitly stated otherwise, the following conditions apply in the present application. The physical properties were determined as described in Merck Liquid Crystals, Physical Properties of Liquid Crystals, Description of the Measurement Methods, ed. W. Becker (Nov 1997).

What is claimed is:

1. A hydrogenated phenanthrene compound of formula (I)

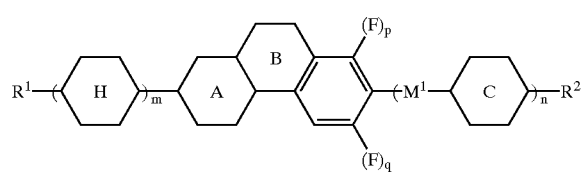

in which:
R¹ is H, C₁₋₁₂-alkyl or C₂₋₈-alkenyl, where, independently in each R¹ one nonterminal —CH₂— group is optionally replaced by —O—, —C(=O)O—, or —OC(=O)— and at least one H is optionally replaced by F,
R² is H, F, C₁₋₁₂-alkyl, C₁₋₁₂-alkoxy, C₂₋₈-alkenyl, or C₂₋₈-alkenyloxy, where, independently in each R², one nonterminal —CH₂— group is optionally replaced by —O— or —C(=O)O— and at least one H is optionally replaced by F,
M¹ is —C(=O)O—, —OC(=O)—, —CH₂O—, —OCH₂—, —C≡C—, —CH₂CH₂ or a single bond,
m, n are each independently zero or 1; m+n being 0 or 1,
p, q are each independently zero or 1; p+q being 1 or 2,

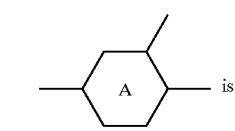 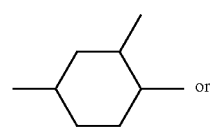

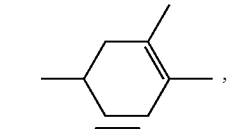 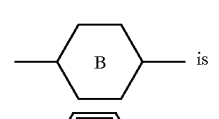

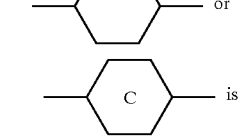 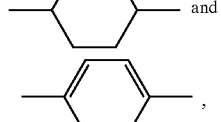

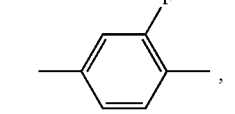 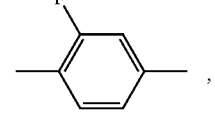

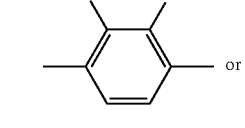 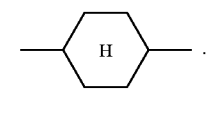

2. A compound according to claim 1, wherein in formula (I), n=0,

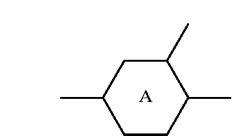 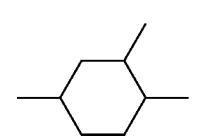

-continued

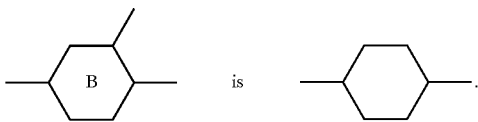

3. A compound according to claim 1, wherein in formula (I), n=0,

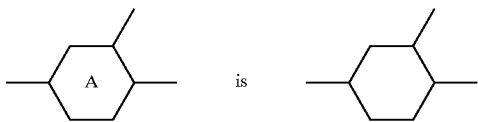

4. A compound according to claim 1, of formulae Ia to Im

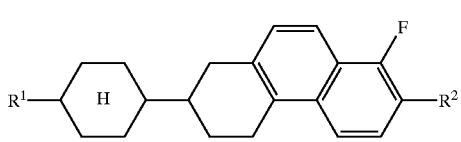
(Ia)

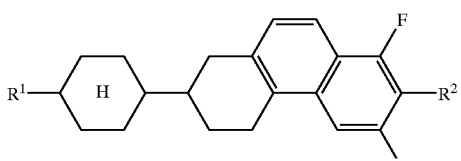
(Ib)

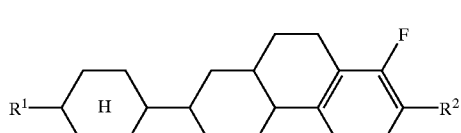
(If)

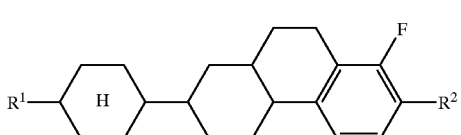
(Ig)

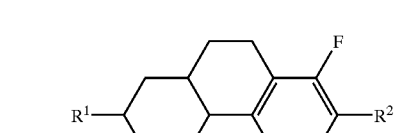
(Ih)

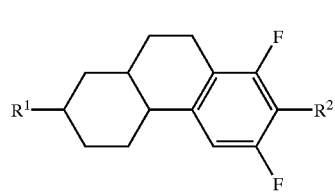
(Ii)

-continued

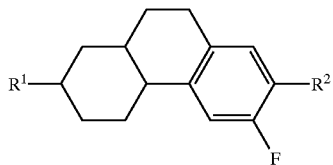
(Ik)

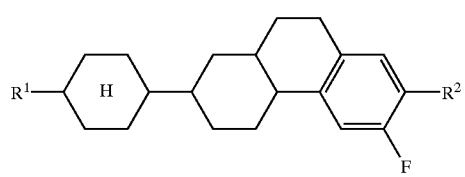
(Im)

in which $R^2$ is:
a) F,
b) $C_{1-2}$-alkyl or $C_{1-2}$-alkoxy in which at least one H is replaced by F, or
c) $C_2$-alkenyl or $C_2$-alkenyloxy in which at least one H is replaced by F.

5. A compound according to claim 4, of formula Ia

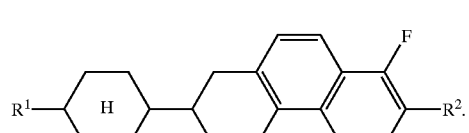
(Ia)

6. A compound according to claim 4, of formula Ib

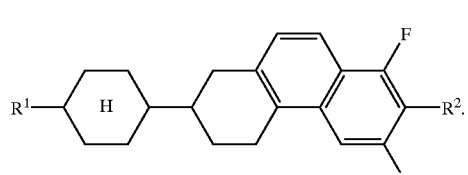
(Ib)

7. A compound according to claim 4, of formula Ic

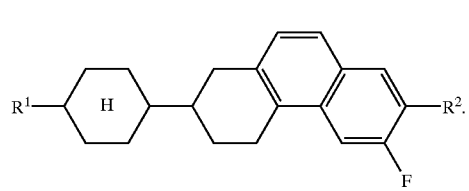
(Ic)

8. A compound according to claim 4, of formula Id

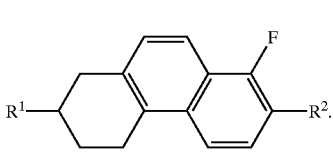
(Id)

9. A compound according to claim 4, of formula Ie

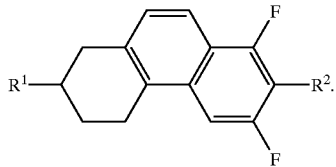
(Ie)

10. A compound according to claim 4, of formula If

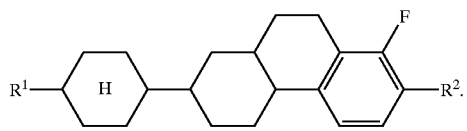
(If)

11. A compound according to claim 4, of formula Ig

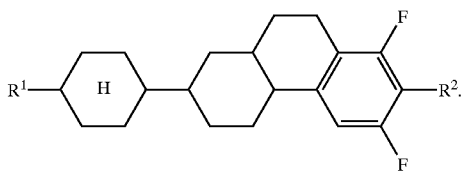
(Ig)

12. A compound according to claim 4, of formula Ih

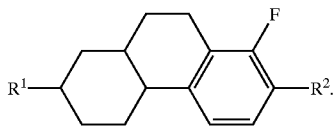
(Ih)

13. A compound according to claim 4, of formula Ii

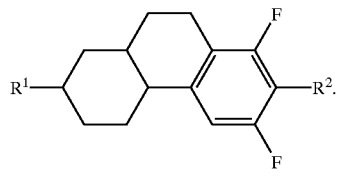
(Ii)

14. A compound according to claim 4, of formula Ik

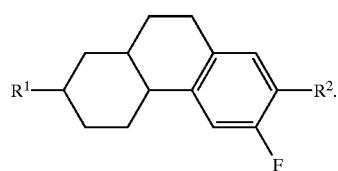
(Ik)

15. A compound according to claim 4, of formula Im

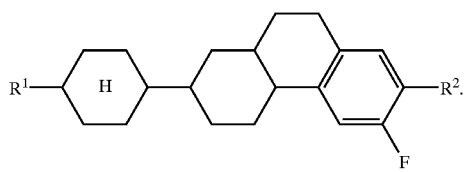
(Im)

16. A liquid-crystal mixture, comprising at least two liquid-cyrstalline compounds, wherein at least one compound is one of formula (I) according to claim 1.

17. A liquid-crystal mixture according to claim 5, comprising 1-40% by weight of at least one compound of formula (I), based on the liquid-crystal mixture.

18. A liquid-crystal mixture according to claim 5, which is nematic or cholesteric.

19. An electrooptical display containing a liquid-crystal mixture according to claim 5.

20. A liquid-crystal mixture, comprising at least two liquid-cyrstalline compounds, wherein at least one compound is one of formula (I) according to claim 2.

21. A liquid-crystal mixture according to claim 9, which is nematic or cholesteric.

22. An electrooptical display containing a liquid-crystal mixture according to claim 9.

23. A liquid-crystal mixture, comprising at least two liquid-cyrstalline compounds, wherein at least one compound is one of formula (I) according to claim 3.

24. A liquid-crystal mixture according to claim 12, which is nematic or cholesteric.

25. An electrooptical display containing a liquid-crystal mixture according to claim 12.

26. A liquid-crystal mixture, comprising at least two liquid-cyrstalline compounds, wherein at least one compound is one of formula (I)a to (I)m according to claim 4.

27. A liquid-crystal mixture according to claim 15, which is nematic or cholesteric.

28. An electrooptical display containing a liquid-crystal mixture according to claim 15.

* * * * *